United States Patent [19]

Lewis et al.

[11] Patent Number: 5,049,656

[45] Date of Patent: Sep. 17, 1991

[54] SEQUENTIAL PEPTIDE AND OLIGONUCLEOTIDE SYNTHESES USING IMMUNOAFFINITY TECHNIQUES

[75] Inventors: William Lewis; Jay Stout; Gino Van Heeke; Dwane E. Wylie; Sheldon M. Schuster, all of Lincoln; Fred W. Wagner, Walton, all of Nebr.

[73] Assignee: Board of Regents of the University of Nebraska, Lincoln, Nebr.

[21] Appl. No.: 288,009

[22] Filed: Dec. 21, 1988

[51] Int. Cl.$^5$ ................................................ C07K 1/04
[52] U.S. Cl. ..................................... 530/334; 530/333
[58] Field of Search .................. 435/91; 530/334, 333; 536/27, 28, 29

[56] References Cited

U.S. PATENT DOCUMENTS 4,689,405 8/1987 Frank et al. ............................ 536/27

OTHER PUBLICATIONS

Stewart, J., et al., *Solid Phase Peptide Synthesis*, Pierce Chemical Company, pp. 41–42, 1984.
Bodanszhy, M., *Principles of Peptide Synthesis*, Springer-Verlag, p. 245, 1984.
Köhler, G. et al., *Nature*, 256; pp. 495–497, 1975.
Ikehara, M. et al., *Advances in Carbohydrate Chemistry and Biochemistry*, 36: 135–212.
Cabrera, K. et al., Med. Sci. Res., 16: 305—310, 1988.
R. B. Merrifield, *J. Amer. Chem. Soc.*, 85, 2149–2154 (1963).
S. L. Beaucage and M. H. Caruthers, *Tet. Lett.*, 22, 1859–1862 (1981).
M. D. Matteucci and M. H. Caruthers, J. Amer. Chem. Soc., 103, 3185–3191 (1981).
L. D. Markley and L. C. Dorman, *Tet. Lett.*, 21, 1787–1790 (1970).
V. A. Efimov et al., *Nucleic Acids Res.*, 13, 3651–3666 (1985).
D. E. Krieger et al., *Proc. Natl. Acad. Sci. U.S.A.*, 73, 3160–3164 (1976).
G. Barany et al., *Int. J. Peptide Protein Res.*, 30, 705–739 (1987).
P. Cuatrecacas, *J. Biol. Chem.*, 245, 3059–3065 (1970).
Biosearch, Inc., *Technical Bulletin No. 9000–01* (1988).
Biosearch, Inc., *Technical Bulletin No. 9000–03*, (1988).
E. R. Doran and R. C. Williams, "Purification of Synthetic Oligonucleotides".
J. D. Haug, *Amer. Biotech. Lab.*, 40–47 (Jan./Feb. 1987).
C. Hoeger et al., *BioChromatography*, 2, 134–142 (1987).
M. Horn and C. Novak, *Amer. Biotech. Lab.*, (no page nos.) (Sep./Oct. 1987).
R. A. Houghten et al., *J. Peptide Protein Res.*, 27, 673–678 (1986).
R. A. Houghten et al., *BioTechniques*, 4, 522–528 (1986).
B. Merrifield, *Science*, 232, 341–347 (1986).
M. P. Reddy and P. J. Voelker, *Int. J. Peptide Protein Res.*, 31, 345–348 (1988).
H. Seliger et al., *Tet. Lett.*, 24, 2115–2118 (1978).
J. P. Tam et al., *J. Am. Chem. Soc.*, 108, 5242–5251 (1986).
M. Wilchek and T. Miron, "Affinity and Carrier-Mediated Peptide Purification," from *Peptides: Structure and Biological Function.*
M. Wilchek and T. Miron, *Perspectives in Peptide Chemistry*, 185–197 (Karger, Basel 1981).
"Operation: Phosphoramidite Synthesis Menu," excerpt from Operational Manual for Vega Coder 300.

*Primary Examiner*—Howard E. Schain
*Assistant Examiner*—Susan M. Perkins
*Attorney, Agent, or Firm*—Merchant, Gould, Smith, Edell, Welter & Schmidt

[57] ABSTRACT

The invention is directed to a method for purifying sequentially synthesized peptides and oligonucleotides by immunoaffinity techniques. Selected products are lapped with an antigenic capping agent and are conjugated with antibodies that are specific for the capping agent.

15 Claims, No Drawings

SEQUENTIAL PEPTIDE AND OLIGONUCLEOTIDE SYNTHESES USING IMMUNOAFFINITY TECHNIQUES

BACKGROUND OF THE INVENTION

Sequential chemical peptide and oligonucleotide syntheses are well established, widely used procedures for producing peptides and oligonucleotides, such as those up to about 40 residues (peptides) and up to 100 residues (oligonucleotides). For peptides, the chemistry involves the specific coupling of the amino terminus of a carboxyl-blocked peptide to the activated carboxyl group of an amino-blocked amino acid. For oligonucleotides, the chemistry involves the specific coupling of the 5'-hydroxyl group of a 3'-blocked nucleotide to an activated 3'-hydroxy group of a 5'-blocked nucleotide.

In their most commonly used forms, developed primarily by Merrifield, *J. Amer. Chem. Soc.*, 85, 2149 (1963) and BeauCage, S. L. and Caruthers, M. H., *Tet. Lett.* 22, 1859–1862 (1981); Beaucage, S. L. and Caruthers, M. H., *J. Amer. Chem. Soc.*, 24, 3184–3191 (1981), these syntheses are accomplished with the peptide or oligonucleotide immobilized on a solid support. An extremely large number of peptides or oligonucleotides can be produced by this methodology. The physical and chemical properties of the peptide or oligonuoleotide products will vary greatly depending on size and composition of the respective amino acids or nucleotides composing these products. Consequently, it is typical to tailor the synthetic techniques to fit the specific product at hand.

In the method of immobilized peptide synthesis, the carboxyl terminal amino acid is bound to a polyvinyl benzene or other suitable insoluble resin. The second amino acid to be added possesses blocking groups on its amino moiety and any side chain reactive groups so that only its carboxyl moiety can react. This carboxyl group is activated with a carbodiimide or other activating agent and then allowed to couple to the immobilized amino acid. After removal of the amino blocking group, the cycle is repeated for each amino acid in the sequence.

The efficiency of the peptide coupling step usually varies from 95–99.9%, depending on the identity of the amino acid and its location in the sequence. During each coupling step, a small portion of the peptides fail to couple the next amino acid. Since these failures occur independently during each coupling step, the amount of correctly sequenced peptide in the final mixture is often less than a major portion. Failed peptides with incorrect sequences (by virtue of amino acid deletions) often accumulate to a significant degree in this mixture.

The same is true of oligonucleotide syntheses. In general, the oligonucleotide synthetic procedure follows the well-established 3'-phosphoramidite schemes devised by Caruthers The 3' terminal base of the desired oligonucleotide is immobilized on an insoluble carrier. The nucleotide base to be added is blocked at the 5' hydroxyl and activated at the 3' hydroxyl so as to cause coupling with the immobilized nucleotide base. Deblocking of the new immobilized nucleotide compound and repetition of the cycle will produce the desired final oligonucleotide.

As is true for the peptides, this nucleotide coupling procedure is not 100% efficient. The immobilized oligonucleotide molecules that do not couple result in oligonucleotides of incorrect sequences. These often cause undesirable reactions if left in mixture with the correct oligonucleotide. Consequently, their separation and removal are mandated even though tedious procedures tailored to each specific synthesis are necessitated.

Separation of the various peptides or oligonucleotides in the respective mixtures produced during synthesis will produce the desired pure, correctly sequenced peptide or oligonucleotide. Conventional separation techniques usually employ high resolution chromatographic procedures such as reverse phase high pressure liquid chromatography, electrophoresis, gel chromatography and the like. These separation method(s) need to resolve peptides or oligonucleotides which differ from each other by as little as one amino acid or nucleotide. The failed peptides and oligonucleotides are compounds having physical and chemical properties very similar to the desired one. Consequently, the separations are difficult to accomplish. Since the compounds synthesized can vary greatly in composition, the monomeric unit sequence and length, the separation methods also are individually tailored to the properties of each mixture. Such separation procedures are difficult to develop, require many man-hours to implement and do not insure absolute homogeneity of the product.

One means for attacking this problem involves increasing the coupling yield. This can be accomplished by performing repeated couplings at each coupling step prior to the next deblocking step. But repeated couplings provide only a partial solution to producing pure peptides or oligonucleotides. The repeated coupling steps expend larger quantities of expensive agents and protected amino acids or nucleotides. In manual synthesis, the coupling yield is monitored at each step before deciding whether to repeat the coupling step, whereas automated synthesis is severely restricted in this respect. Moreover, some peptides or oligonucleotides fail to couple completely during the chain elongation because the large size of the activated amino acid or nucleotide prevents access to some of the peptides or oligonucleotide molecules on the resin. Therefore, these methods are severely limited in scope.

Another means for attacking this problem involves "capping". This method reduces the total number of incorrectly sequenced or "failed" peptides or oligonucleotides in the synthetic mixture. To cap, the failed peptides or oligonucleotides are reacted with a capping agent which prevents the failed peptide or oligonucleotide from participating in subsequent coupling reactions (for peptides, see Merrifield, *J. Amer. Chem. Soc.* (1963) 2149; Markley and Dorman, *Tetrahedron Letters* (1970), 1787; for oligonucleotides, see Efimov, V.A., Chakhmakhcheva, O. G., and Ovchimikov, V.A. *Nucleic Acids Res.* 13, 3651 (1985)).

As applied to peptides, capping can be accomplished because the extended (i.e., coupled) peptide possesses a blocked amino group at the N-terminus while the failed peptides possess a free N-terminus amino group. Once the failed peptide is capped, it is unavailable for further coupling steps. The result is a mixture of capped failed peptides of different lengths and the correctly extended peptide without a cap.

As applied to oligonucleotides, capping can be accomplished because the failed oligonucleotide contains a free 5'-hydroxyl group. Capping with an irreversible agent that reacts with hydroxyl groups will prevent further reaction of this failed side product. The cap will not react in any subsequent steps of the oligonucleotide synthetic procedure.

A modification of the capping strategy employs a capping agent which changes the chemical or physical properties of the failed peptides or oligonucleotides (Penke and Birr *Justus Liebigs Ann. Chem.*, 1999 (1974), and Krieger et al., *Proc Nat. Acad. Sci.* 3160 (1976)). Such modifications augment the chemical and physical differences between the correctly extended peptide or oligonucleotide and the failed peptides or oligonucleotides. These differences tend to aid separation.

Nevertheless, these capping methods for reducing the contamination of synthetically produced peptides or oligonucleotides have drawbacks. No matter what the capping agent, the overall physical characteristics of the peptides or oligonucleotides usually determine their physical and chemical behavior. The resulting separations remain dependent upon the overall physical and chemical behavior of the peptides or oligonucleotides. Very tedious and time consuming separations result because the overall properties of the desired product and side products are much the same.

Therefore, it is an object of the invention to develop a synthetic method for the preparation of peptides and oligonucleotides that yields pure product. Another object is to develop a method that avoids time-consuming separation techniques. Yet another object is to base this method upon a capping technique.

SUMMARY OF THE INVENTION

These and other objects are achieved by the present invention which is directed to a sequential peptide or oligonucleotide synthetic method that employs immunoaffinity techniques.

According to one embodiment of the method of the invention, failed peptides or oligonucleotides of the sequential synthesis are capped with an agent that is highly antigenic. Specific antibodies to this capping agent, which can be immobilized upon a solid support or may be in solution, conjugate with and remove the antigenically capped, failed peptides or oligonucleotides from the reaction mixture.

According to another embodiment of the method of the invention, the reverse capping procedure also allows isolation and purification of the desired peptide or oligonucleotide. Here, the desired, correctly sequenced peptide or oligonucleotide is antigenically capped as a last step of the synthetic sequence, while the failed peptides or oligonucleotides are capped with other reagents during each cycle of the synthetic sequence. Immune affinity conjugation With specific antibodies for the antigenic capping agent removes the desired peptide or oligonucleotide from the reaction mixture. Dissociation of the conjugate then releases the desired peptide or oligonucleotide.

According to the invention, the peptide capping agent is an aromatic acylating agent that is reactive toward free amino groups of peptides and is capable of causing an immune response either alone or when reacted with a haptene. Especially preferred peptide capping agents are fluorescamine and its derivatives, and substituted or unsubstituted compounds of phthalic anhydride, benzoyl halide or naphthoyl halide wherein the substituents are mono-, di- or tri-nitro; mono-, di- or tri-alkoxy; mono-, di- or tri-cyano; or mono-, di-, or tri-carboxyl; and halide is fluoride, chloride, bromide or iodide.

According to the invention, the oligonucleotide capping agent is an acylating, phosphorylating or carbamylating agent that is reactive toward free 5'-hydroxyl groups of failed oligonucleotides and is capable of causing an immune response either alone or when reacted with a carrier. Especially preferred oligonucleotide capping agents are substituted or unsubstituted aromatic isocyanates, dialkoxytriazoylphosphine, aliphatic acid halides of 2 to 10 carbons and substituted or unsubstituted compounds of phthalic anhydride, benzoyl halide or naphthoyl halide wherein the substituents are mono-, di- or tri-nitro; mono-, di- or tri-alkoxy; mono-, di- or tri-cyano; or mono-, di-, or tri-carboxyl; and halide is fluoride, chloride, bromide or iodide.

For the peptide reverse capping procedure, the antigenic cap can be any of the peptide N-block protecting groups that are stable toward acidic and other of the usual N-block removal techniques, such as anhydrous HF treatment, aqueous acid treatment and hydrogenation, but can be removed with aqueous base. These include, for example, 9(2-sulfo)fluorenylmethyloxycarbonyl (SULFmoc) or fluorenylmethyloxycarbonyl (Fmoc) groups as well as other groups that react with amines and can be cleaved by basic treatment. In this scheme, the failed peptides are capped with one of the aromatic acylating agents mentioned above. Immunoaffinity conjugation then removes the desired peptide.

For the oligonucleotide reverse capping procedure, 5'-hydroxyl oligonucleotide protecting groups such as the dimethyltrityl group, the dansyl group aromatic sulfonyl halides, and aromatic and aliphatic silating groups, can serve as an antigenic group. In this scheme, acetyl or similar acylating groups mentioned in the foregoing oligonucleotide capping section are used to cap the failed oligonucleotides. Immunoaffinity conjugation then removes the desired oligonucleotides.

Double separations are also within the invention. Differing antigenic caps for both the desired products and failed side products are introduced at the appropriate steps of the synthetic sequence. Immunoaffinity separation with two different antibodies, which select for the desired and failed products, provides selection.

The specific antibodies according to the invention are polyclonal or monoclonal antibodies produced by immunosensitizing a mammal with an antigen composed of compounds produced by binding the capping agent to a carrier. Known screening techniques for polyclonal antibody production yield the desired polyclonal antibodies. Screening for a capping agent immune response and cross screening for the absence of a carrier, amino acid or nucleotide immune response produces the selective monoclonal antibodies.

According to the invention the specific antibodies may be immobilized upon a solid support or they may be maintained in solution during the cap-antibody complexing process. Separation in the former situation may be accomplished by washing or other support flushing techniques. In the latter, it may be accomplished by immune complement precipitation.

The invention is also directed to an agent kit containing the antigenic capping agent, the immunoaffinity material with specific antibodies and the appropriate buffers and agents for utilization in a sequential peptide or oligonucleotide synthesis.

DETAILED DESCRIPTION OF THE INVENTION

Chemically synthesized peptides of up to about 6 thousand molecular weight and pieces of single stranded DNA of 20 to 100 bases have a variety of commercial, experimental, medical and diagnostic uses. In the research environment, peptides and oligonucleotides can be used a probes and reagents. For example, a DNA probe the isolation of DNA fragments from nuclear material has great utility in the field of recombinant DNA technology. Synthetic DNA can also be used as a clinical diagnostic probe for specific viruses or cells. Peptides or oligonucleotides labeled with fluorescent probes also have utility as therapeutic agents to detect diseases, foreign bodies and genetic disorders. As pharmaceuticals, peptides control physiological processes and hence are of great value in the treatment of disease and injury. But the presence of failed peptides or oligonucleotides in mixture with the desired ones may result in toxic, antigenic, unknown or undesirable activities. Consequently, there is a great need to prepare such peptides and oligonucleotides in substantially pure form.

Nevertheless, one of the key draw-backs of synthetic peptide or oligonucleotide production is the seemingly impossible task of purification of the final product. Currently, high performance liquid chromatography HPLC procedures are employed. These procedures are not readily adaptable to large samples and are not completely effective in removing all contaminants from a sample. The present invention addresses and solves these difficulties.

The method of the present invention is a purification procedure based upon the biospecificity of antibody-antigen reactions. It involves antigenically capping those selected peptides or oligonucleotides of a synthetic mixture that are to be removed by antigenic conjugation. In one version of the method, those selected compounds have failed to incorporate the amino acid or nucleotide unit being coupled during a cycle of a sequential synthesis. Here, the antigenically capped peptides or oligonucleotides constitute impurities in the mixture and are easily removed by immunoaffinity techniques according to the invention. By this means of purification, the correctly synthesized, uncapped peptide or oligonucleotide is obtained in purified form.

In another version of the method, those selected compounds are the reverse of the failed peptides or oligonucleotides. Here, only the desired product (peptide or oligonucleotide) is antigenically modified while the failed side products are capped with other reagents that do not conjugate under the specific conditions of the immunoaffinity technique being employed.

The purification steps of the method are dependent on the specificity of the immobilized antibody for the capping group and are independent of both the chemical and the physical characteristics of the peptides or oligonucleotides. The failed peptides or oligonucleotides, for the reverse procedure, the desired ones, are removed by a single immunoaffinity reaction respectively that is common to all failed peptides or oligonucleotides regardless of their sequence, or, for the reverse procedure, that is unique to the correct peptide or oligonucleotide. Hence, a simple, single purification is made and the final product Will not contain any peptides or oligonucleotides containing failed sequences.

PEPTIDE CAPPING AGENTS

According to the invention, the agent for capping failed peptides is designed so that specific antibodies toward the capping group (monoclonal or polyclonal) can be produced. The capping agent has been generally characterized in the foregoing section. In an especially preferred embodiment of the invention, this capping agent is an aromatic acyl halide such as dinitrobenzoyl chloride (DNB), nitrophthalic anhydride or fluorescamine. These agents produce the acylated derivatives of the targeted peptides in the reaction mixture. The acylation terminates any further reaction of the failed peptides in subsequent coupling reactions.

The failed peptide capping agent in general has several properties. It is highly reactive toward amino groups and is small enough to have access to the resin bound peptide. These features insure that all of the failed peptides are capped. The capping agent is also antigenic so that antibodies may be produced which bind the capped peptides. To insure that the correctly synthesized, uncapped peptide is not bound by the antibodies to the capping group, the capping group is not antigenically similar to any of the functional groups normally found in peptides. Further properties include the capping group stability under the conditions for synthesis of the peptide and for removal of the protective groups attached to the peptide during synthesis. Finally, the capping agent is inexpensive. This expediently enables use of large excesses of the agent and insures complete reaction.

Generally, the peptide synthetic sequence practiced during the performance of the invention follows well-known procedures for peptide-peptide coupling and peptide functional group protection. See, for example, George Barany, et al., In. J. Peptide Protein Res., 30, 705-739 (1987), the disclosure of which is incorporated herein by reference. Foresight shows that reactions to remove these protecting and blocking groups should not also remove the capping agent. Consequently, the protective and blocking groups are chosen so that they can be removed in the presence of a stabilized capping agent. Examples of such protecting and blocking groups include aromatic sulfonyl groups, benzyl groups, pyridyl sulfenyl groups, benzyloxymethyl groups, and alkyloxycarbonyl groups, as well as others listed at Table 1 of the Barany article.

During this synthesis, the correctly formed peptides are not derivatized by the capping agent since the amino group of these peptides possesses any of the well-known blocking groups. After the completion of the synthetic sequence, the correct peptide and all the capped failed peptides are deprotected by standard procedures. The capping groups on the failed peptides are not removed by these methods. The result is a mixture of peptides in which all peptides, except the correctly synthesized sequence, are present as the capped derivatives.

This mixture of peptides is preferably combined with an immunoaffinity resin containing immobilized antibodies (monoclonal or polyclonal) against the cap functional group. The capped peptides are specifically bound to this resin while the correctly synthesized peptide remains unbound. The solution containing the correctly formed peptide is separated from the resin containing the failed peptides or peptides of incorrect sequence.

The reverse capping procedure calls for antigenically capping the correctly sequenced peptide. Here, the usual N-block, C-block and pendant functional group protecting agents that can be removed with HF, acid hydrolysis or other non-basic techniques form the basis for the usual synthetic sequence manipulations. Reversible amine peptide capping groups such as 9(2-sulfo)-fluorenylmethyloxycarbonyl (SULFmoc) or Fluoroenylmethyloxycarbonyl (Fmoc) that are removable by base treatment constitute the antigenic capping agents for the amino terminus of the desired peptide. These capping agents can be added to the desired peptide as the amino protecting group of the N-terminal amino acid. These capping agents are stable to the normal N-block deprotection procedures, i.e., HF, but are easily removed by aqueous alkali. The immunoaffinity techniques employing antibodies to these groups then will be directed to the desired peptide, while the failed peptides that are capped with other reagents are washed away or otherwise removed.

OLIGONUCLEOTIDE CAPPING AGENTS

The agents for capping failed and desired oligonucleotides are designed so that specific antibodies toward them (monoclonal or polyclonal) can be produced. These agents have been generally characterized in the foregoing section.

The capping agent allows purification of the desired oligonucleotide from all the undesired oligonucleotides. As this technique is applied to both versions of the method of the invention, monoclonal or polyclonal antibodies to the capping agent or to the standard 5' blocking group are generated. In the first instance, immunoaffinity conjugation will bind the failed oligonucleotide to the immunoaffinity support. In the second, (the reverse procedure) the desired oligonucleotide will be bound.

In general, the capping agent for failed oligonucleotides has several properties. It is highly reactive toward hydroxyl groups and is small enough to have access to the resin bound oligonucleotide. These features insure that all of the failed oligonucleotides are capped. The capping agent is also antigenic so that antibodies may be produced which bind the capped oligonucleotides. To insure that the correctly synthesized, uncapped oligonucleotide is not bound by the antibodies to the capping group, the capping group is not antigenically similar to any of the functional groups normally found in oligonucleotides. Further properties include the capping group stability under the conditions for synthesis of the oligonucleotide and for removal of the protective groups attached to the oligonucleotide during synthesis. Finally, the capping agent is inexpensive. This expediently enables use of large excesses of the agent and insures complete reaction.

Generally, the oligonucleotide sequential synthesis practiced in accordance with the invention follows the well-known techniques laid out by Caruthers, cited above and reviewed by S. A. Narang, in "Synthesis and Applications of DNA and RNA", Academic Press, N.Y., 1987, the disclosure of which is incorporated herein by reference. Appropriate 3'-and 5'-hydroxy protecting and activating groups as well as pendant function group protective agents are incorporated in this synthesis with the synthetic logic expressed by those in the art, such as Narang.

Within the oligonucleotide synthesis and purification, according to the invention, the immunoaffinity technique requires only one separation step. Where the immunoaffinity separation is directed toward the failed oligonucleotide, the antigenic capping agent characterized above is reacted with the failed oligonucleotide at the end of the synthetic cycle and before the 5'-blocking group is removed. Selection of the appropriate capping agent will take into account the needed differing reactivities of the capping, protecting and blocking groups. Removal of one or more, but not all, of these groups pursuant to the logic of the synthetic sequence guides this selection. Especially preferred capping agents for failed oligonucleotides include DNB, aromatic isocyanates and aromatic acylating groups.

Where the immunoaffinity separation is directed toward the correctly sequenced oligonucleotide, a standard 5' capping group, such as acetic anhydride or another acylating group caps the failed oligonucleotides pursuant to known procedures (see, e.g., Narang cited above). The correctly sequenced oligonucleotide will be capped with a dimethyltrityl, dansyl or other ether 5'-blocking group as mentioned above. The only oligonucleotide designed to conjugate with the antibodies will be the correctly sequenced one. Thus, this procedure is applicable to any automated synthetic solid-phase oligonucleotide synthesis procedure.

GENERAL TECHNIQUES

(a) Capping of Failed Peptides

The synthesis of the peptides is accomplished by conventional synthetic sequence methods using known N- and C-blocking and activating agents respectively such as t-BOC and FMOC; carbodimide, or a acyl halide and symmetric anhydrides. Preferably, peptide synthesis occurs on a solid support. The capping of the peptides which do not couple the added amino acid at each step requires additional steps be added to each synthetic cycle. Following the reaction of the activated amino acid with the immobilized peptide, the resulting product mixture is reacted with an aromatic acyl halide such as dinitrobenzoyl chloride. This compound is a potent acylating agent which reacts with the remaining $NH_2$ groups to form the acyl derivative of the failed peptides. The agents are removed and the t-BOC protecting groups on the remaining peptides are removed as in the usual methodology.

b) Capping of Desired Peptide

Subsequent to the practice of the foregoing failed peptide capping procedure, which in this event can be accomplished by agents such as acetic anhydride, the desired peptide is capped with an antigenic capping agent that does not de-cap under usual acidic deblocking and deprotecting conditions but will under basic conditions.

c) Cappinq of Failed Nucleotides

The synthesis of the oligonucleotides is accomplished by conventional synthetic sequence methods including binding on a solid support. The capping of failed oligonucleotide that does not couple with the added activates nucleotide also requires an additional step. Following the reaction of the 3'-activated, 5'-blocked nucleotide with the immobilized deprotected oligonucleotide, the product mixture is reacted with an aromatic or aliphatic acyl halide such as dinitrobenzoyl chloride, phosphorylating agents or carbamylating agents such as phenyl isocyanate. These compounds are potent reactants which readily combine with the 5'-hydroxyl groups of the unreacted, immobilized oligonucleotide. Oxidation of the phosphite group of the capped nucleotide produces a phosphate group. The resulting capped side product is stable to the remainder of the reaction sequence.

d) Capping of Desired Oligonucleotides

In the reverse procedure, the failed oligonucleotides can be capped with an acetyl group (from acetic anhydride or acetyl chloride). The final step of the synthesis generates a 5' standard blocking group (e.g. with trityl or dansyl) upon the correctly sequenced oligonucleotide which distinguishes it from the acetyl capped, failed oligonucleotides.

e) Preparation of Polyclonal antibodies

Polyclonal antibodies to the antigenic capping agent such as the dinitrobenzoyl (DNB) group are prepared by injecting capped Keyhole Limpet Hemocyanin (e.g. capped with DNB or other cap-KLH) into rabbits. The capping agent is coupled to the haptene carrier such as KLH under the usual protein acylating conditions. After rabbit serum antibody titer is maximal (6-8 weeks) the IgG fraction is purified from the blood serum by precipitation with ammonium sulfate at 33-45% of saturation. The anti-cap antibodies (i.e. those that complex with cap) are further purified by immunoaffinity chromatography against one or more immobilized cap carriers. For example, purification against immobilized cap-KLH, then against immobilized cap-Bovine serum albumin (BSA coupled with the capping agent) and immobilized underivatized KLH is an appropriate method. Antibodies which bind to cap-KLH and cap-BSA, but not to underivatized KLH, are selected for use.

f) Preparation of Monoclonal Antibodies

Alternatively, monoclonal antibodies can be used; however, in this case monoclonal antibodies may be specific for particular capped amino acids. Thus, clones of monoclonal antibodies must be screened with all 20 capped amino acids as well as any modified amino acids or amino acid analogs used for particular applications. All 20 amino acids plus any analogs or modified amino acids used for the synthesis of the peptide must bind to the antibody or mixture of antibodies selected for use.

For preparation of Monoclonal Antibodies to nucleotides and for each of the agents to be used as immunizing agents, there will be 4 possible nucleotide derivatives to which monoclonal antibodies will be synthesized. Thus in each instance it will be necessary to immunize separate mice with 5'-DMT or 5'-cap derivatives of each of the four 2-deoxyribonucleotides found in DNA namely, adenine, guanosine cytosine and thymidine.

The antigenic capping agent is covalently bound to keyhole limpet hemocyanin (KLH). The suspension is used to immunize a host animal such as a mouse, preferably by injection. The laboratory strain of mouse designated BALB/c is particularly preferred.

Antibody-producing cells of the immunized host are collected by removing the host's spleen and preparing a suspension of spleen cells. The spleen cells are fused with cells of a myeloma cell line, preferably of the same animal species of the immunized host, and typically in the presence of a cell fusion promoter such as polyethylene glycol to form hybridoma cells. The hybridoma cells are diluted and cultured in a medium which does not promote the growth of unfused cells.

The monoclonal antibodies produced and secreted by the hybridomas are thereafter assayed for the ability to bind immunologically with the capping agent used for immunization. The preferred assay method in this context is an enzyme-linked immunoabsorbent assay. See, for example, E. Engvall, "Methods In Enzymology", Vol. 70, p. 419–438, Academic Press, New York 1980 for a general discussion of the enzyme-linked immunoabsorbent assay, the disclosure of which is incorporated herein by reference. Screening for the hybridomas will be performed With capping agent bound to each of the 20 amino acids or 4 nucleotides so that antibodies selected bind only to the capping agent regardless of which amino acid or nucleotide residue constitutes the site for attachment of the capping agent.

g) Immunoaffinity Chromatography of Peptides or Oligonucleotides

The anti-cap antibodies are immobilized to a resin by conventional methods. See for example Cuatrecasas, J. Biol. Chem., 245, 3059 (1970) the disclosure of which is incorporated herein by reference. Briefly, the antibodies in buffered aqueous solution are mixed with an activated resin to form covalent bonds or strong complexes between the antibodies and resin. Typical covalent activating agents for the resin include cyanogen bromide, N-hydroxysuccinimide, carbonyl diimidazole and toluene sulfonyl chloride as well as others discussed by Cuatrecasas. Typical resins include Sepharose (a modified polydextran made by Pharmacia Inc. Sweden), agarose resin and other sugar derived resins. The covalent activating agents are reacted with the resin to form links for covalent attachment of the antibodies to the resin. Strongly complexing resins such as ion exchange resins can also be used.

The anti-cap antibody resin is then used to remove the capped peptides or nucleotides from the peptide or oligonucleotide mixture. The lyophilized mixture, containing the antigenically capped peptides or oligonucleotides (failed or desired) and the remaining peptides or oligonucleotides, is dissolved in a buffer solution (pH 6.5–8.0). The antibody resin is equilibrated in the same buffer and packed into a conventional chromatography column. The sample is added to the column and the column is washed with buffer until the major peptide or oligonucleotide band is eluted. The antigenically capped peptides or oligonucleotides remain bound to the resin and can be eluted by washing the resin in a buffered solution at pH 9.5–10.5. The antibody resin can be reused by extensive washing in the original buffer.

The Column effluent is monitored continuously at either 210 nm or 260 nm wavelengths where peptides and nucleotides possess high molar absorptivities, respectively.

h) Precipitation of Complexed Antibodies

As an alternative to immobilized antibody separation, the specific antibodies in media can be added to the appropriate antigenically capped mixture of materials. Precipitation of the antibody-antigen complex with complement or with base or acid buffer will then remove the capped materials. Other known methods for separation of media borne antigen-antibody complexes can also be employed.

The utility of the method is conferred by a combination of the addition of an antigenic capping group to the failed or desired peptides or oligonucleotides and the use of an immunoaffinity resin directed specifically toward the capping group for separation of these peptides or oligonucleotides.

These components are described in the following examples which illustrate the application of the method in both manual and automated synthetic protocols. The examples are intended as illustrations only and is not meant to limit the invention thereto.

In the examples, acronyms are given for solvents and agents. The full name is given the first time a particular solvent or agent is indicated.

EXAMPLE 1

Peptide Synthesis

Leu-enkephylin, a peptide hormone produced by the pituitary gland, was synthesized by standard manual methods and by the same method modified to include the present invention. The sequence of leu-enkephalin is Tyr-Gly-Gly-Phe-Leu.

Manual Synthesis of Leu-Enkephalin

Synthesis of leu-enkephylin by the conventional methods involved the following steps:

1) The starting resin, N-tBOC-Leucyl polystyrene is placed in the reaction vessel.
2) The resin is washed with dry dichloromethane (DCM).
3) The tBOC protecting group is removed by incubating the resin in 10ml of 20% triflouroacetic acid (TFA) in DCM for 28 minutes.
4) The resin is washed in DCM, then in 5% triethylamine in DCM.
5) The resin is suspended in 10 ml DCM.
6) A five-fold excess of the next amino acid, N-tBOC-Phe, is added to the resin along with an equimolar amount (relative to amino acid) of dicyclohexylcarbodiimide.
7) The mixture is incubated for 45 minutes at room temperature.
8) Steps 2-6 are repeated for each amino acid in the sequence substituting the appropriately blocked amino acid in step 6. The amino acids used are:
cycle 2; N-tBOC-Gly
cycle 3; N-tBOC-Gly
cycle 4; 0-(2-Br-0Z-N-tBOC-Tyr)
9) The resin is washed with DCM
10) 1.5 ml of 2:1 thioanisole: ethanedithiol (EDT) is added to the resin.
11) The mixture is stirred for 10 minutes.
12) One ml of TFA is added and the mixture was stirred for 10 minutes.
13) 100ul of trifluoromethanesulfonic Acid (TFMSA) is slowly added.
14) The mixture is stirred for 1 hour at room temperature.
15) The mixture is filtered through a sintered glass funnel into 25ml of methyl t-butyl ether.
16) The reaction vial is washed 3 times with 0.5 ml TFA. The wash solution is filtered through the sintered glass funnel and collected as in step 14.
17) The combined filtrates are incubated at 4° for 15 minutes.
18) The precipitated peptide is collected by filtration through a clean sintered glass funnel and washed with methyl t-butyl ether.
19) The peptide is dissolved in 0.1% TFA and lyophylized.
20) The peptide is washed by three cycles of suspension in water and then dried by lyophylized.

Manual Synthesis of DNB-capped Leu-Enkephalin

The twenty step procedure given above was followed to synthesize the DNB capped peptide except that the following modifications were made.

Following the procedure described in step 7, the following steps are added in each cycle.

i) The resin is washed with DMF.
ii) The resin is incubated with a tenfold excess of dinitrobenzoyl chloride (relative to the peptide) in DMF.
iii) The resin is washed with DMF.

The DNB capping group is not removed by this procedure.

EXAMPLE 2

Bradykinin, a vasoactive peptide secreted by the liver, was synthesized by using a Dupont Coupler 2200 automated synthesizer using the protocol supplied by the manufacturer and the same method modified to incorporate the present invention. The protocols used are summarized below and along with the modifications made to incorporate the capping steps. The sequence of bradykinin is Arg-Pro-Pro-Gly-Phe-Ser-Pro-Phe-Arg.

Automated Synthesis of Bradykinin

1) The resin, N-tBOC-Arginyl-phenylacetoamidomethylpolystyrene (PAM) is placed in the reaction vessel.
2) The resin is washed with 60% TFA in DCM.
3) The t-BOC protecting group is removed by incubation of the resin with 10 ml of 60% TFA in DCM for 15 minutes.
4) The resin is washed three times with 10 ml of DCM.
5) The resin is washed twice with 10 ml of 10% Diisopropylethylamine.
6) The resin is washed 3 times with 10 ml DMF
7) The second amino acid, N-tBOC-Phe, is dissolved in DMF.
8) The amino acid is activated and attached to the resin-bound peptide according to the Instrument manufacturer,s protocol. This protocol varies, depending on the identity of the amino acid. Activation is accomplished by incubation with diisopropylcarbodiimide and hydroxybutyltriozole in DMF.
9) Following the coupling, the resin is washed with 7 ml DMF.
10) Steps 3-9 are repeated for each amino acid in the sequence. The protected amino acids used in step 7 for subsequent cycles of the bradykinin synthesis are:
cycle 2; N-tBOC-Pro
cycle 3; 0-Benzyl-N-tBOC-Ser
cycle 4; N-tBOC-Phe
cycle 5; N-tBOC-Gly
cycle 6; N-tBOC-Pro
cycle 7; N-tBOC-Pro
cycle 8; tosyl-N-tBOC-Arg
11) After the synthesis is complete the resin is incubated at 0° C. with freshly distilled HF, containing 10% thioanisole, to remove the peptide from the resin and remove all blocking groups.
12) Residual HF is removed from the product by vacuum distillation. The peptide is precipitated with diethylether and extracted into 10% acetic acid. The acetic acid is removed by sublimation to yield the crude peptide powder.

Automated Synthesis of DNB-Capped Bradykinin

1) The synthesis of the capped peptide follows the procedure for the uncapped peptide except that the following steps are added in each synthetic cycle following step 8.
i) The resin is washed three times with 10 ml DMF.
ii) The resin is incubated with 10% DNBCL IN DMF at room temperature for 20 minutes.
2) The DNB capping group is not removed by HF deblocking in step 11.

Affinity Chromatography of Peptides

The peptides produced are all subjected to immunoaffinity chromatography on a column containing the immunoaffinity resin. The antibody used was a polyclonal anti-DNB antibody produced in a rabbit. The resin used was cyanogen bromlde treated Sepharose gel brand of modified polydextran (Pharmacia, Sweden). The following steps were applied to the purification of eaoh peptide.
1) The resin is packed into a plastic chromatography column.
2) The column is equilibrated with an 0.1 M solution of $K_2HPO_4$ buffer (pH 7).
3) The peptide mixture is dissolved in the same buffer.
4) The peptide solution is applied to the column.
5) The column is eluted with the buffer.
6) The effluent is monitored at 210 nm.
7) The major absorbing peak is collected.
8) The column is regenerated by washing with 10% sodium carbonate followed by extensive washing in the pH 7 buffer.
9) The peptide solution collected is lyophylized to yield the purified peptide.

EXAMPLE 3

General Procedure for Preparation of Oligonucleotide

1. Hydroxyl (3') attachment to the insoluble support.
The 5' DMT blocked nucleoside desired to be at the 3' terminus of the synthetic oligonucleotide is attached to controlled pore glass by a spacer arm. Resins, containing each of the four possible nucleosides, can be purchased commercially.
2. Removal of the immobile 5-DMT group.
Generally 5% dichloroacetic acid in dichloromethane is used to hydrolyze the DMT group from the 5'-terminus of the growing oligonucleotide.
3. Chain elongation.
In this step a 3'-activated 5'-DMT blocked nucleotide is allowed to react with the immobile free 5'-group of the growing oligonucleotide. The 3' activation group is 3'-(beta)-cyanoethylphosphoramidite. This step is usually 98% complete; however, the 2% that does not react will be available for reaction in the next cycle and will produce an oligonucleotide with a base deleted from the desired sequence. At this point in the synthesis these free 5' hydroxyls of the 2% failed oligonucleotide are "capped" with an acylating agent.
4. Capping.
At this point, the capping method can be used to generate an antigenic capped oligonucleotide. The capping agent is an acylating agent such as 2,4-dinitrobenzoyl chloride (DNBCL). The capped oligonucleotide will consequently possess an 2,4-dinitrobenzoyl group instead of an acetyl group. These capped sequences are no longer available for chain elongation.

5. Oxidation.
The phosphite group of the nucleotide is oxidized to a phosphate group with iodine.
6. Further chain elongation by repeating steps 2 through 5.
7. Deprotection and cleavage.
The solid phase oligonucleotide is incubated in concentrated ammonium hydroxide during which time it is cleaved from the resin by base hydrolysis This step also facilitates the removal of the cyanoethyl protecting groups from the phosphate groups.
8. Removal of base protecting groups.
The bases adenine guanosine and cytosine are protected with benzoyl groups (A and C) or isobutyryl groups (G) These groups removed by further reaction the oligonucleotide in concentrated ammonium hydroxide for 12 hr at 55° C.

Purification of Capped Oligonucletoides.

The soluble oligonucleotide possessing the DMT blocking groups (as well as those blocking groups removed in step 8) are eluted through an immunoaffinity resin. The resin possesses immobilized antibodies to either the DMT group or to the DNB (dinitrobenzoyl group). In the former case the desired 5' blocked oligonucleotide will adhere to the resin and all the undesired capped oligonucleotides will elute. The DMT oligonucleotide can be eluted from the resin by conventional procedures, or the resin can be treated with acid as in Step 2 to cleave the DMT from the oligonucleotide where upon the latter will elute form the affinity column.

If the oligonucleotide has been capped with DNBC1 then the product from Step 7 or Step 8 is passed over an immunoaffinity column containing bound antibody to DNB. Under these conditions all capped oligonucleotides will bind to the column and the desired product will elute. The column can be washed with dilute acid or base to elute the DNB capped oligonucleotides.

Separation of Oligonucleotides by Immunoaffinity Chromatography

Lyophilized synthetic oligonucleotides are dissolved in phosphate buffered saline, pH 7.0 (PBS). The antibody column is also equilibrated in PBS buffer. The sample is added to the column, then the column is washed with PBS. If the immunoaffinity support is specific for DMT the major DMT-oligonucleotide will remain bound to the resin and the capped oligonucleotides which do not contain DMT will elute. The DMT-oligonucleotide can be eluted as described for the DNB resin or the column can be eluted with acid as in Step 2 of the procedure hydrolyze DMT from oligonucleotide, thus releasing it from the resin.

Palindromic Oligonucleotide Synthesis

Following the foregoing procedure, a palindromic 18 nucleotide long oligonucleotide is synthesized using a Vega Coder 300 automated synthesizer. The sequence of the oligonucleotide is 5' GAATTCGGATCCGAATTC 3'. This sequence has two EcoRI sites at either end and a BamHl site in the middle.

Synthesis of 18 nucleotide long oligonucleotide by convention methods involved the following steps:
1. The 5' dimethoxytrityl (DMT) blocked benzylcytosine-B-cyanoethyl phosphoramidite at the 3' terminus was purchased in a form that was already attached to controlled pore glass by a spacer arm.

2. The DMT protecting group was removed from the 5' hydroxyl group by 5% dichloroacetic acid in dichloromethene.

3. The 150 uL of 5' DMT thymidine-B-cyanoethyl phosphoramidate was then mixed with 150 uL of tetrazole. The coupling reaction was then allowed to occur for 3 minutes.

4. The 5' hydroxyl groups of unreacted cytosine were then capped with 150 uL of acetic anhydride and 150 uL of n-methylimidazole. The capping reaction was complete in 30 seconds.

5. The 3-' phosphite formed is then oxidized to the phosphate by the reaction with an iodine solution for 30 seconds.

6. The steps 2-5 are repeated for each nucleotide in the sequence substituting the appropriately blocked amino acid in step 3. The nucleotides used are:
Cycle 2; 5'-0-DMT-T-B-cyanoethyl phosphoramidite (DMT-T)
Cycle 3; 5'-0-DMT-Adenosine-B-cyanoethyl phosphoramidite (DMT-A)
Cycle 4; DMT-A
Cycle 5; 5'-DMT-lBu-dG-B-cyanoethyl phosphoramidite (DMT-G)
Cycle 6; 5'-DMT-Bz-dC-B-cyanoethyl phosphoramidite (DMT-C)
Cycle 7; DMT-C
Cycle 8; DMT-T
Cycle 9; DMT-A
Cycle 10; DMT-G
Cycle 11; DMT-G
Cycle 12; DMT-C
Cycle 13; DMT-T
Cycle 14; DMT-T
Cycle 15; DMT-A
Cycle 16; DMT-A
Cycle 17; DMT-G 7. The resin is reacted with concentrated ammonium hydroxide at 50° C. for 16 hours.

8. Vortex sample and allow resin to settle.

9. Decant liquid from resin.

10. Vacuum centrifuge to dryness.

A Palindromic Synthesis of DNB-capped Oligonucleotide

The procedure described above is repeated with the following modifications:

1. The acetic anhydride in step 4 is replaced by 10% solution of DNBCl.

2 After step 6 for cycle 17 step 2 is included.

The mixture of DNB capped palindromic failed oligonucleotides and the correctly sequenced palindrome can then be chromatographed on an immunoaffinity column of rabbit anti-DNB antibody coupled to Sepharose brand of modified polydextran as described above for peptide chromatography. Elution with appropriate buffer yields the desired product.

We claim:

1. A method for the synthesis of a polypeptide which comprises:
   (a) preparing a C-terminus blocked peptide of at least one amino acid in length;
   (b) reacting an N-blocked, C-activated amino acid with the C-terminus blocked peptide to produce a mixture of an extended peptide and an unreacted peptide;
   (c) adding an antigenic N-terminus capping agent to the mixture to antigenically cap the unreacted peptide, wherien the antigenic N-terminus capping agent is an aromatic acylating capping agent that reacts with amine groups;
   (d) combining the mixture of antigenically capped unreacted peptide and extended peptide with antibodies that are selective for the antigenic cap; and
   (e) isolating the extended peptide thereby producing the polypeptide.

2. A method according to claim 1, wherein the C-terminus blocked peptide, chain extended peptide, unreacted peptide and antigenically capped unreacted peptide are immobilized on a solid support and the solid support is removed just prior to step (d).

3. a method according to claim 1, or 2, further comprising:
   repeating steps (a) through (c) one or more times;
   removing the N-block on the extended peptide after each repetition of step (c) to form a new C-terminus blocked peptide for each repetition of step (a); and,
   reacting the same or a different N-blocked, C-activated 4. A method according to claim 3, wherein the aromatic acylating agent is fluorescamine and its derivatives or a substituted or unsubstituted phthalic anhydride, benzoyl halide or naphthoyl halide, the substituents being selected from the group consisting of mono-, di- or tri-nitro; mono-, di- or tri-methoxy; mono-, di- or tri-cyano; and mono-, di- or tri-carboxy; and the halide being fluoro, chloro, bromo and iodo.

5. A method for the synthesis of a polypeptide which comprises:
   (a) preparing a C-terminus immobilized peptide of at least one amino acid in length, said C-terminus immobilized peptide being immobilized upon a support;
   (b) reacting an N-blocked, C-activated amino acid with the C-terminus immobilized peptide to produce a mixture of immobilized extended peptide and immobilized unreacted peptide;
   (c) adding an antigenic N-terminus capping agent to the mixture to antigenically cap the immobilized unreacted peptide, wherein the antigenic N-terminus capping agent is an aromatic acylating capping agent that reacts with amine groups;
   (d) removing the N-block from the immobilized extended peptide to produce a new C-terminus immobilized peptide;
   (e) repeating steps (a) throughout (d) with the new C-terminus immobilized peptide and the same or different N-blocked, C-activated amino acid until the desired polypeptide sequence in immobilized form is produced;
   (f) removing the desired polypeptide and the antigenically capped unreacted peptides from the support;
   (g) combining the desired polypeptide and antigenically capped unreacted peptides with antibodies that are selective for the antigenic cap to form a conjugated mixture; and
   (h) removing the desired polypeptide from the conjugated mixture.

6. A method according to claim 5 wherein blocking groups for pendant functional moieties of the amino acid residues of the peptides are also removed in step (f).

7. A method for the synthesis of a polypeptide which comprises:
   conducting a series of reactions which couple together the amino acids of the polypeptide;

at the completion of each coupling reaction, antigenically capping the N-terminus of any unreacted peptide side product that did not undergo the coupling reaction, the capping being conducted with an antigenic aromatic acylating capping agent that reacts with amine groups, thereby producing antigenically capped side products; and removing the antigenically capped side products by their conjugation with antibodies that are immunospecific for the antigenic cap.

8. A method according to claim 7, wherein the removing step is performed at the end of the series of coupling steps.

9. A method for separating a mixture of a synthesized N-blocked polypeptide and N-unblocked unreacted peptide side products which comprises:

antigenically capping the N-terminus of the N-unblocked unreacted peptide side products with an N-terminus antigenic aromatic acylating capping agent to form antigenically capped side products, and conjugating the antigenically capped side products with antibodies that are immunospecific for the antigenic cap.

10. A method for separating a mixture of a synthesized N-blocked polypeptide, and N-unblocked unreacted peptide side products which comprises:

capping the N-terminus of the N-blocked unreacted peptide side products with an N-terminus capping agent, employing SULFmoc, Fmoc or an acid stable, base labile acylating group as the N-block of the sequentially synthesized N-blocked polypeptide and conjugating the resulting mixture with antibodies that are immunospecific for the SULFmoc, Fmoc or acid stable, base labile acylating group.

11. A method according to claim 10, further comprising employing an antigenic capping agent to cap the unreacted peptide side products, wherein the antigenic capping agent is an aromatic acylating capping agent that reacts with amine groups, and, in addition to conjugating with the antibodies that are immunospecific for the SULFmoc, Fmoc or acid stable, base labile acylating group, further conjugating the resulting mixture with antibodies that are immunospecific for the N-terminus antigenic cap.

12. A method according to claim 1, 5, 7, 9, 10 or 11 wherein the antibodies are polyclonal and selectively immunoreact with the antigenic cap.

13. A method according to claim 1, 5, 7, 9, 10 or 11 wherein the antibodies are monoclonal and selectively immunoreact with the antigenic cap.

14. A method according to claim 1, 5, 7, 9, 10 or 11 wherein the antibodies are immobilized upon a solid support.

15. A kit for antigenically capping peptides, which comprises;

a solution of antigenic capping agent in inert solvent wherein the antigenic capping agent is an aromatic acylating capping agent suitable for reaction with amino groups; and antibodies in a buffered medium wherein the antibodies are immunoselective for the antigenic cap.

* * * * *

UNITED STATES PATENT AND TRADEMARK OFFICE
CERTIFICATE OF CORRECTION

PATENT NO. :   5,049,656
DATED      :   September 17, 1991
INVENTOR(S):   William Lewis et al.

It is certified that error appears in the above-identified patent and that said Letters Patent is hereby corrected as shown below:

Col. 16

Claim 3, line 22, after "activated" please insert
    --amino acid at each repetition of step (b)--.

Col. 17

Claim 10, line 27, please delete "N-blocked" and
    insert --N-unblocked--.

Signed and Sealed this

Eighth Day of June, 1993

Attest:

MICHAEL K. KIRK

Attesting Officer        Acting Commissioner of Patents and Trademarks